(12) United States Patent
Lee et al.

(10) Patent No.: US 7,399,831 B2
(45) Date of Patent: Jul. 15, 2008

(54) TARGETED DELIVERY OF BIOLOGICAL FACTORS USING SELF-ASSEMBLING PEPTIDE NANOFIBERS

(75) Inventors: Richard T. Lee, Weston, MA (US); Michael E. Davis, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 132 days.

(21) Appl. No.: 11/254,805

(22) Filed: Oct. 21, 2005

(65) Prior Publication Data

US 2006/0088510 A1 Apr. 27, 2006

Related U.S. Application Data

(60) Provisional application No. 60/621,464, filed on Oct. 25, 2004.

(51) Int. Cl.
*A61K 38/00* (2006.01)
*C07K 17/00* (2006.01)
(52) U.S. Cl. ............................ 530/350; 514/2; 530/300
(58) Field of Classification Search ....................... None
See application file for complete search history.

(56) References Cited

U.S. PATENT DOCUMENTS 5,670,483 A 9/1997 Zhang et al. .................. 514/14
6,548,630 B1 4/2003 Zhang et al. ................. 530/300

OTHER PUBLICATIONS

Segers and Lee, "Local delivery of proteins and the use of self-assembling peptides", Drug Discovery Today 12(13/14):561-568 (2007).*
Chan, et al., Effect of Streptavidin Affinity Mutants on the Integrin-Independent Adhesion of Biotinylated Endothelial Cells, *Biomaterials* 24:559-570 (2003).
Davis, et al., "Injectable Self-Assembling Peptide Nanofibers Create Intramyocardial Microenvironments for Endothelial Cells," *Circulation* 111:442-450 (2005).
Davis, et al., "Custom Design of the Cardiac Microenvironment with Biomaterials," *Circ. Res.* 97:8-15 (2005).
Fraidenraich, et al., "Rescue of Cardiac Defects in *ID* Knockout Embryos by Injection of Embryonic Stem Cells," *Science* 306:247-252 (2004).
Li, et al., Overexpression of Insulin-Like Growth Factor-1 in Mice Protects from Myocyte Death after Infraction, Attenuating Gentricular Dilation, Wall Stress, and Cardiac Hypertrophy, *J. Clin. Invest.* 100:1991-1999 (1997).
Kofidis, et al., "Insulin-Like Growth Factor Promotes Engraftment, Differentiation, and Functional Improvement after Transfer of Embryonic Stem Cells for Myocardial restoration," *Stem Cells* 22:1239-1245 (2004).

Livnah, et al., Three-Dimensional Structures of Avidin and the Avidin-Biotin Complex, *Proc. Natl. Acad. Sci. USA.* 90:5076-5080 (1993).
Neish, et al., "Direct Visualization of Ligand-Protien Interactions Using Atomic Force Microscopy," *British J. Pharmacol.* 135:1943-1950 (2002).
Ohno, et al., "Cell-Specific, Multidrug Delivery System Using Streptavidin-Protien A Fusion Protien," *Biochem. Mol. Med.* 58:227-233 (1996).
Palmen, et al., "Cardiac Remodeling after Mycardial Infarction Is Impaired in IGF-1 Deficient Mice," *Cardiovasc. Res.* 50:516-524 (2001).
Pugliese, et al., "Three-Dimensional Structure of the Tetragonal Crystal Form of Egg-White Avidin in its Functional Complex with Biotin at 2-7 A Resolution," *J. Mol. Biol.* 231:698-710 (1993).
Smith, et al., "Redirected Infection of Directly Biotinylated Recombinant Adenovirus Vectors Through Cell Surface Receptors and Antigens," *Proc. Natl. Acad. Sci. USA* 96:8855-8860 (1999).
Stayton, et al., "Control of Protein-Ligand Recognition Using a Stimuli-Responsive Polymer," *Nature* 378:472-474 (1995).
Torella, et al., "Cardiac Stem Cell and Myocyte Aging, Heart Failure, and Insulin-Like Growth Factor-1 Overexpression," *Circ. Res.* 94:514-524 (2004).
Vasan, et al., "Serum Insulin-Like Growth Factor 1 and Risk for Heart Failure in Elderly Individuals without a Previous Myocardial Infraction: The Framingham Heart Study," *Ann. Intern. Med.* 139:642-648 (2003).
Zhang, et al., "Fabrication of Novel Biomaterials through Molecular Self-Assembly," *Nature Biotech* 21:1171-1178 (2003).
Zhang, et al., "Spontaneous Assembly of Self-Complementary Oligopeptide to Form a Stable Macroscopic Membrane," *Proc. Natl. Acad. Sci. USA* 90:3334-3338 (1993).
Zhang, et al., "Design of Nanostructured Biological Materials through Self-Assembly of Peptides and Protiens," *Curr. Opin. Chem. Biol* 6:865-871 (2002).
International Search Report for PCT/US2005/037955, published May 4, 2006.
International Preliminary Examination Report for PCT/US2005/037955, issued Aug. 28, 2007.

* cited by examiner

*Primary Examiner*—Robert B. Mondesi
*Assistant Examiner*—Anand U Desai
(74) *Attorney, Agent, or Firm*—Michael A. Sanzo; Law Offices of Michael A. Sanzo, LLC

(57) ABSTRACT

The present invention is directed to methodology that allows a variety of compounds to be attached to self-assembling peptides using biotin/streptavidin linkages. The peptides can be used to form a biologically compatible membrane that promotes the growth and differentiation of cells. The attached therapeutic agents can be used to promote this process and the gel along with the growing cells can be implanted at a site in vivo where tissue repair is needed. Alternatively, membranes can be used for culturing cells in vitro or can be used for delivering drugs in vivo in the absence of seeded cells.

17 Claims, No Drawings

SEQUENCE LISTING

<160> NUMBER OF SEQ ID NOS: 89

<210> SEQ ID NO 1
<211> LENGTH: 16
<212> TYPE: PRT
<213> ORGANISM: Artificial
<220> FEATURE:
<223> OTHER INFORMATION: synthetic sequence designed for self assembly

<400> SEQUENCE: 1

Ala Lys Ala Lys Ala Glu Ala Glu Ala Lys Ala Lys Ala Glu Ala Glu
1               5                   10                  15

<210> SEQ ID NO 2
<211> LENGTH: 16

```
<212> TYPE: PRT
<213> ORGANISM: artificial
<220> FEATURE:
<223> OTHER INFORMATION: synthetic sequence designed for self assembly

<400> SEQUENCE: 2

Ala Lys Ala Glu Ala Lys Ala Glu Ala Lys Ala Glu Ala Lys Ala Glu
1               5                   10                  15

<210> SEQ ID NO 3
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 3

Glu Ala Lys Ala Glu Ala Lys Ala Glu Ala Lys Ala Glu Ala Lys Ala
1               5                   10                  15

<210> SEQ ID NO 4
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 4

Lys Ala Glu Ala Lys Ala Glu Ala Lys Ala Glu Ala Lys Ala Glu Ala
1               5                   10                  15

<210> SEQ ID NO 5
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 5

Ala Glu Ala Lys Ala Glu Ala Lys Ala Glu Ala Lys Ala Glu Ala Lys
1               5                   10                  15

<210> SEQ ID NO 6
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 6

Ala Asp Ala Asp Ala Arg Ala Arg Ala Asp Ala Asp Ala Arg Ala Arg
1               5                   10                  15

<210> SEQ ID NO 7
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 7

Ala Arg Ala Asp Ala Arg Ala Asp Ala Arg Ala Asp Ala Arg Ala Asp
1               5                   10                  15

<210> SEQ ID NO 8
<211> LENGTH: 16
<212> TYPE: PRT
```

```
<213> ORGANISM: artificial
<220> FEATURE:
<223> OTHER INFORMATION: synthetic sequence designed for self assembly

<400> SEQUENCE: 8

Asp Ala Arg Ala Asp Ala Arg Ala Asp Ala Arg Ala Asp Ala Arg Ala
1               5                   10                  15

<210> SEQ ID NO 9
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 9

Arg Ala Asp Ala Arg Ala Asp Ala Arg Ala Asp Ala Arg Ala Asp Ala
1               5                   10                  15

<210> SEQ ID NO 10
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 10

Ala Asp Ala Arg Ala Asp Ala Arg Ala Asp Ala Arg Ala Asp Ala Arg
1               5                   10                  15

<210> SEQ ID NO 11
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 11

Ala Arg Ala Asp Ala Lys Ala Glu Ala Arg Ala Asp Ala Lys Ala Glu
1               5                   10                  15

<210> SEQ ID NO 12
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 12

Ala Lys Ala Glu Ala Arg Ala Asp Ala Lys Ala Glu Ala Arg Ala Asp
1               5                   10                  15

<210> SEQ ID NO 13
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 13

Ala Arg Ala Lys Ala Asp Ala Glu Ala Arg Ala Lys Ala Asp Ala Glu
1               5                   10                  15

<210> SEQ ID NO 14
<211> LENGTH: 16
<212> TYPE: PRT
<213> ORGANISM: artificial
```

<220> FEATURE:
<223> OTHER INFORMATION: synthetic sequence designed for self assembly

<400> SEQUENCE: 14

Ala Lys Ala Arg Ala Glu Ala Asp Ala Lys Ala Arg Ala Asp Ala Glu
1               5                   10                  15

<210> SEQ ID NO 15
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 15

Ala Gln Ala Gln Ala Gln Ala Gln Ala Gln Ala Gln Ala Gln Ala Gln
1               5                   10                  15

<210> SEQ ID NO 16
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 16

Val Gln Val Gln Val Gln Val Gln Val Gln Val Gln Val Gln Val Gln
1               5                   10                  15

<210> SEQ ID NO 17
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 17

Tyr Gln Tyr Gln Tyr Gln Tyr Gln Tyr Gln Tyr Gln Tyr Gln Tyr Gln
1               5                   10                  15

<210> SEQ ID NO 18
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 18

His Gln His Gln His Gln His Gln His Gln His Gln His Gln His Gln
1               5                   10                  15

<210> SEQ ID NO 19
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 19

Ala Asn Ala Asn Ala Asn Ala Asn Ala Asn Ala Asn Ala Asn Ala Asn
1               5                   10                  15

<210> SEQ ID NO 20
<211> LENGTH: 16
<212> TYPE: PRT
<213> ORGANISM: artificial
<220> FEATURE:

```
<223> OTHER INFORMATION: synthetic sequence designed for self assembly

<400> SEQUENCE: 20

Val Asn Val Asn Val Asn Val Asn Val Asn Val Asn Val Asn Val Asn
1               5                   10                  15

<210> SEQ ID NO 21
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 21

Tyr Asn Tyr Asn Tyr Asn Tyr Asn Tyr Asn Tyr Asn Tyr Asn Tyr Asn
1               5                   10                  15

<210> SEQ ID NO 22
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 22

His Asn His Asn His Asn His Asn His Asn His Asn His Asn His Asn
1               5                   10                  15

<210> SEQ ID NO 23
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 23

Ala Asn Ala Gln Ala Asn Ala Gln Ala Asn Ala Gln Ala Asn Ala Gln
1               5                   10                  15

<210> SEQ ID NO 24
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 24

Ala Gln Ala Asn Ala Gln Ala Asn Ala Gln Ala Asn Ala Gln Ala Asn
1               5                   10                  15

<210> SEQ ID NO 25
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 25

Val Asn Val Gln Val Asn Val Gln Val Asn Val Gln Val Asn Val Gln
1               5                   10                  15

<210> SEQ ID NO 26
<211> LENGTH: 16
<212> TYPE: PRT
<213> ORGANISM: artificial
<220> FEATURE:
<223> OTHER INFORMATION: synthetic sequence designed for self assembly
```

```
<400> SEQUENCE: 26

Val Gln Val Asn Val Gln Val Asn Val Gln Val Asn Val Gln Val Asn
1               5                   10                  15

<210> SEQ ID NO 27
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 27

Tyr Asn Tyr Gln Tyr Asn Tyr Gln Tyr Asn Tyr Gln Tyr Asn Tyr Gln
1               5                   10                  15

<210> SEQ ID NO 28
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 28

Tyr Gln Tyr Asn Tyr Gln Tyr Asn Tyr Gln Tyr Asn Tyr Gln Tyr Asn
1               5                   10                  15

<210> SEQ ID NO 29
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 29

His Asn His Gln His Asn His Gln His Asn His Gln His Asn His Gln
1               5                   10                  15

<210> SEQ ID NO 30
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 30

His Gln His Asn His Gln His Asn His Gln His Asn His Gln His Asn
1               5                   10                  15

<210> SEQ ID NO 31
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 31

Ala Lys Ala Gln Ala Asp Ala Lys Ala Gln Ala Asp Ala Lys Ala Gln
1               5                   10                  15

Ala Asp

<210> SEQ ID NO 32
<211> LENGTH: 18
<212> TYPE: PRT
<213> ORGANISM: artificial
<220> FEATURE:
```

-continued

```
<223> OTHER INFORMATION: synthetic sequence designed for self assembly

<400> SEQUENCE: 32

Val Lys Val Gln Val Asp Val Lys Val Gln Val Asp Val Lys Val Gln
1               5                   10                  15

Val Asp

<210> SEQ ID NO 33
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 33

Tyr Lys Tyr Gln Tyr Asp Tyr Lys Tyr Gln Tyr Asp Tyr Lys Tyr Gln
1               5                   10                  15

Tyr Asp

<210> SEQ ID NO 34
<211> LENGTH: 18
<212> TYPE: PRT
<213> ORGANISM: artificial
<220> FEATURE:
<223> OTHER INFORMATION: synthetic sequence designed for self assembly

<400> SEQUENCE: 34

His Lys His Gln His Asp His Lys His Gln His Asp His Lys His Gln
1               5                   10                  15

His Asp

<210> SEQ ID NO 35
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 35

Arg Ala Arg Ala Asp Ala Asp Ala Arg Ala Arg Ala Asp Ala Asp Ala
1               5                   10                  15

<210> SEQ ID NO 36
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 36

Arg Ala Asp Ala Arg Gly Asp Ala Arg Ala Asp Ala Arg Gly Asp Ala
1               5                   10                  15

<210> SEQ ID NO 37
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 37

Arg Ala Glu Ala Arg Ala Glu Ala Arg Ala Glu Ala Arg Ala Glu Ala
1               5                   10                  15
```

```
<210> SEQ ID NO 38
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 38

Lys Ala Asp Ala Lys Ala Asp Ala Lys Ala Asp Ala Lys Ala Asp Ala
1               5                   10                  15

<210> SEQ ID NO 39
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 39

Ala Glu Ala Glu Ala His Ala His Ala Glu Ala Glu Ala His Ala His
1               5                   10                  15

<210> SEQ ID NO 40
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 40

Phe Glu Phe Glu Phe Lys Phe Lys Phe Glu Phe Glu Phe Lys Phe Lys
1               5                   10                  15

<210> SEQ ID NO 41
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 41

Leu Glu Leu Glu Leu Lys Leu Lys Leu Glu Leu Glu Leu Lys Leu Lys
1               5                   10                  15

<210> SEQ ID NO 42
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 42

Ala Glu Ala Glu Ala Lys Ala Lys Ala Glu Ala Glu Ala Lys Ala Lys
1               5                   10                  15

<210> SEQ ID NO 43
<211> LENGTH: 12
<212> TYPE: PRT
<213> ORGANISM: artificial
<220> FEATURE:
<223> OTHER INFORMATION: synthetic sequence designed for self assembly

<400> SEQUENCE: 43

Ala Glu Ala Glu Ala Glu Ala Glu Ala Lys Ala Lys
1               5                   10

<210> SEQ ID NO 44
```

```
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 44

Lys Ala Lys Ala Lys Ala Lys Ala Glu Ala Glu Ala Glu Ala Glu Ala
1               5                   10                  15

<210> SEQ ID NO 45
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 45

Ala Glu Ala Glu Ala Glu Ala Glu Ala Lys Ala Lys Ala Lys Ala Lys
1               5                   10                  15

<210> SEQ ID NO 46
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 46

Arg Ala Arg Ala Arg Ala Arg Ala Asp Ala Asp Ala Asp Ala Asp Ala
1               5                   10                  15

<210> SEQ ID NO 47
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 47

Ala Asp Ala Asp Ala Asp Ala Asp Ala Arg Ala Arg Ala Arg Ala Arg
1               5                   10                  15

<210> SEQ ID NO 48
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 48

Asp Ala Asp Ala Asp Ala Asp Ala Arg Ala Arg Ala Arg Ala Arg Ala
1               5                   10                  15

<210> SEQ ID NO 49
<211> LENGTH: 16
<212> TYPE: PRT
<213> ORGANISM: artificial
<220> FEATURE:
<223> OTHER INFORMATION: synthetic sequence designed for self assembly

<400> SEQUENCE: 49

His Glu His Glu His Lys His Lys His Glu His Glu His Lys His Lys
1               5                   10                  15

<210> SEQ ID NO 50
<211> LENGTH: 20
```

```
<212> TYPE: PRT
<213> ORGANISM: artificial
<220> FEATURE:
<223> OTHER INFORMATION: synthetic sequence designed for self assembly

<400> SEQUENCE: 50

Val Glu Val Glu Val Glu Val Glu Val Glu Val Glu Val Glu Val Glu
1               5                   10                  15

Val Glu Val Glu
            20

<210> SEQ ID NO 51
<211> LENGTH: 20
<212> TYPE: PRT
<213> ORGANISM: artificial
<220> FEATURE:
<223> OTHER INFORMATION: synthetic sequence designed for self assembly

<400> SEQUENCE: 51

Arg Phe Arg Phe Arg Phe Arg Phe Arg Phe Arg Phe Arg Phe Arg Phe
1               5                   10                  15

Arg Phe Arg Phe
            20

<210> SEQ ID NO 52
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 52

Ala Lys Ala Lys Ala Glu Ala Glu
1               5

<210> SEQ ID NO 53
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 53

Arg Ala Arg Ala Asp Ala Asp Ala
1               5

<210> SEQ ID NO 54
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 54

Arg Ala Asp Ala Arg Ala Asp Ala
1               5

<210> SEQ ID NO 55
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 55

Ala Glu Ala Glu Ala Lys Ala Lys
```

```
1               5

<210> SEQ ID NO 56
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 56

Lys Ala Glu Ala
1

<210> SEQ ID NO 57
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 57

Glu Ala Lys Ala
1

<210> SEQ ID NO 58
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 58

Lys Ala Glu Ala
1

<210> SEQ ID NO 59
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 59

Ala Glu Ala Lys
1

<210> SEQ ID NO 60
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 60

Ala Asp Ala Asp Ala Arg Ala Arg
1               5

<210> SEQ ID NO 61
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 61

Ala Arg Ala Asp
1
```

```
<210> SEQ ID NO 62
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 62

Asp Ala Arg Ala
1

<210> SEQ ID NO 63
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 63

Arg Ala Asp Ala
1

<210> SEQ ID NO 64
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 64

Ala Asp Ala Arg
1

<210> SEQ ID NO 65
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 65

Ala Arg Ala Asp Ala Lys Ala Glu
1               5

<210> SEQ ID NO 66
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 66

Ala Lys Ala Glu Ala Arg Ala Asp
1               5

<210> SEQ ID NO 67
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 67

Ala Arg Ala Lys Ala Asp Ala Glu
1               5
```

-continued

```
<210> SEQ ID NO 68
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 68

Lys Ala Arg Ala Glu Ala Asp Ala
1               5

<210> SEQ ID NO 69
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 69

Ala Asn Ala Gln
1

<210> SEQ ID NO 70
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 70

Ala Gln Ala Asn
1

<210> SEQ ID NO 71
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 71

Val Asn Val Gln
1

<210> SEQ ID NO 72
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 72

Val Gln Val Asn
1

<210> SEQ ID NO 73
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 73

Tyr Asn Tyr Gln
1
```

```
<210> SEQ ID NO 74
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 74

Tyr Gln Tyr Asn
1

<210> SEQ ID NO 75
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 75

His Asn His Gln
1

<210> SEQ ID NO 76
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 76

His Gln His Asn
1

<210> SEQ ID NO 77
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 77

Ala Lys Ala Gln Ala Asp
1               5

<210> SEQ ID NO 78
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 78

Val Lys Val Gln Val Asp
1               5

<210> SEQ ID NO 79
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 79

Tyr Lys Tyr Gln Tyr Asp
1               5

<210> SEQ ID NO 80
```

```
<211> LENGTH: 6
<212> TYPE: PRT
<213> ORGANISM: artificial
<220> FEATURE:
<223> OTHER INFORMATION: synthetic sequence designed for self assembly

<400> SEQUENCE: 80

His Lys His Gln His Asp
1               5

<210> SEQ ID NO 81
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 81

Arg Ala Asp Ala Arg Gly Asp Ala
1               5

<210> SEQ ID NO 82
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 82

Arg Ala Glu Ala
1

<210> SEQ ID NO 83
<211> LENGTH: 4
<212> TYPE: PRT
<213> ORGANISM: artificial
<220> FEATURE:
<223> OTHER INFORMATION: synthetic sequence designed for self assembly

<400> SEQUENCE: 83

Lys Ala Asp Ala
1

<210> SEQ ID NO 84
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 84

Ala Glu Ala Glu Ala His Ala His
1               5

<210> SEQ ID NO 85
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 85

Phe Glu Phe Glu Phe Lys Phe Lys
1               5

<210> SEQ ID NO 86
<211> LENGTH: 8
```

```
<212> TYPE: PRT
<213> ORGANISM: artificial
<220> FEATURE:
<223> OTHER INFORMATION: synthetic sequence designed for self assembly

<400> SEQUENCE: 86

Leu Glu Leu Glu Leu Lys Leu Lys
1               5

<210> SEQ ID NO 87
<211> LENGTH: 12
<212> TYPE: PRT
<213> ORGANISM: artificial
<220> FEATURE:
<223> OTHER INFORMATION: synthetic sequence designed for self assembly

<400> SEQUENCE: 87

Ala Glu Ala Glu Ala Glu Ala Glu Ala Lys Ala Lys
1               5                   10

<210> SEQ ID NO 88
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 88

His Glu His Glu His Lys His Lys
1               5

<210> SEQ ID NO 89
<211> LENGTH: 8
<212> TYPE: PRT
<213> ORGANISM: artificial
<220> FEATURE:
<223> OTHER INFORMATION: synthetic sequence designed for self assembly

<400> SEQUENCE: 89

Ala Arg Ala Arg Ala Asp Ala Asp
1               5
```

TARGETED DELIVERY OF BIOLOGICAL FACTORS USING SELF-ASSEMBLING PEPTIDE NANOFIBERS

CROSS REFERENCE TO RELATED APPLICATIONS

The present application claims priority to, and the benefit of, U.S. provisional application 60/621,464, filed on Oct. 25, 2004. The contents of this prior application are hereby incorporated by reference in their entirety.

FIELD OF THE INVENTION

The present invention is directed to methods for non-covalently attaching factors to membranes formed by self-assembling peptides. Membranes that have been altered in this manner can be used to support the growth and differentiation of cells both in vitro and in vivo. The membranes can also be used for the long-term delivery of therapeutic agents at sites of implantation.

BACKGROUND OF THE INVENTION

Certain peptides are capable of self assembly when incubated in the presence of low concentrations of monovalent metal cations (U.S. Pat. Nos. 5,670,483; 6,548,630). Assembly results in the formation of a gel-like membrane that is non-toxic, non-immunogenic and relatively stable to proteases. Once formed, membranes are stable in serum, aqueous solutions and cell culture medium. They can be made under sterile conditions, are capable of supporting the growth of cells and are slowly digested when implanted in an animal's body. These characteristics make the membranes well suited as devices for drug delivery and as scaffolds for promoting the growth of cells in vivo.

In order to fully realize the biological potential of membranes, a method must be available for anchoring growth factors and therapeutic agents to the self-assembled peptides. Although compounds can simply be enmeshed in the peptide matrix, the highly permeable nature of the membranes will tend to lead to the rapid loss of such compounds in vivo. Ideally, factors should be attached to membranes in a way that is resistant to diffusion, that does not disrupt the structure of the membrane and that can be applied a wide range of compounds.

SUMMARY OF THE INVENTION

The present invention is based upon the development of a method for linking factors to membranes formed by self-assembling peptides. The method involves non-covalently attaching the factor to a small percentage of the peptides using biotin/avidin linkages and then allowing the peptides to form a membrane. The method can be applied to any compound capable of attachment to biotin or streptavidin, including growth factors, hormones, therapeutic agents and diagnostic compounds.

In its first aspect, the invention is directed to a biologically compatible peptide membrane made of self-assembling peptides. The term "biologically compatible" indicates that the membranes are non-toxic and can be implanted in a patient without triggering an immune response. The self-assembling peptides should be 12-200 amino acids in length and have alternating hydrophobic and hydrophilic amino acids. In addition, the peptides should be complementary (i.e., they should be able to form ionic or hydrogen bonds with one another) and structurally compatible (i.e., the bound peptide chains should maintain a distance from one another that does not vary by more than about three angstroms throughout their length). Between 0.1% and 10% (and preferably 0.5-5%) of the peptides that assemble into the membrane are bound to a factor (e.g., a diagnostic agent, therapeutic agent, growth factor etc.) by a biotin/streptavidin linkage. As used herein, the term "streptavidin" is intended to include avidin as well.

The use of biotin and streptavidin for linking molecules is well known in the art and standard methodology can be used for forming linkages between the self-assembling peptides and attached factors. In order to prevent steric interference between the biotin/streptavidin groups and the peptides, there should be a spacer included between the two. One or more spacers may also be included between the attached factor and biotin. The spacer can take the form of 1-15 (preferably 1-10) fatty acids or 1-15 (preferably 1-10) amino acids and should separate the attached factor from the peptide by at least an additional 12 angstroms and by no more than an additional 250 angstroms. Methodology for incorporating spacers of this type is well known in the art.

In preferred embodiments, the self-assembling peptides used in membranes are between 12 and 24 amino acids in length, have about 1% attached to a factor, and are homogeneous. The term "homogeneous" as used in this context indicates that all of the peptides forming the biologically compatible membrane are identical. The term "heterogeneous" refers to non-identical peptides that are used to form membranes. Specific peptides that may be used in the membranes described above include:

| | |
|---|---|
| AKAKAEAEAKAKAEAE,; | (SEQ ID NO:1) |
| AKAEAKAEAKAEAKAE,; | (SEQ ID NO:2) |
| EAKAEAKAEAKAEAKA,; | (SEQ ID NO:3) |
| KAEAKAEAKAEAKAEA,; | (SEQ ID NO:4) |
| AEAKAEAKAEAKAEAK,; | (SEQ ID NO:5) |
| ADADARARADADARAR,; | (SEQ ID NO:6) |
| ARADARADARADARAD,; | (SEQ ID NO:7) |
| DARADARADARADARA,; | (SEQ ID NO:8) |
| RADARADARADARADA,; | (SEQ ID NO:9) |
| ADARADARADARADAR,; | (SEQ ID NO:10) |
| ARADAKAEARADAKAE,; | (SEQ ID NO:11) |
| AKAEARADAKAEARAD,; | (SEQ ID NO:12) |
| ARAKADAEARAKADAE,; | (SEQ ID NO:13) |
| AKARAEADAKARADAE,; | (SEQ ID NO:14) |
| AQAQAQAQAQAQAQAQ,; | (SEQ ID NO:15) |
| VQVQVQVQVQVQVQVQ,; | (SEQ ID NO:16) |
| YQYQYQYQYQYQYQYQ,; | (SEQ ID NO:17) |
| HQHQHQHQHQHQHQHQ,; | (SEQ ID NO:18) |
| ANANANANANANANAN,; | (SEQ ID NO:19) |
| VNVNVNVNVNVNVNVN,; | (SEQ ID NO:20) |
| YNYNYNYNYNYNYNYN,; | (SEQ ID NO:21) |

-continued

| | |
|---|---|
| HNHNHNHNHNHNHNHN, ; | (SEQ ID NO:22) |
| ANAQANAQANAQANAQ, ; | (SEQ ID NO:23) |
| AQANAQANAQANAQAN, ; | (SEQ ID NO:24) |
| VNVQVNVQVNVQVNVQ, ; | (SEQ ID NO:25) |
| VQVNVQVNVQVNVQVN, ; | (SEQ ID NO:26) |
| YNYQYNYQYNYQYNYQ, ; | (SEQ ID NO:27) |
| YQYNYQYNYQYNYQYN, ; | (SEQ ID NO:28) |
| HNHQHNHQHNHQHNHQ, ; | (SEQ ID NO:29) |
| HQHNHQHNHQHNHQHN, ; | (SEQ ID NO:30) |
| AKAQADAKAQADAKAQAD, ; | (SEQ ID NO:31) |
| VKVQVDVKVQVDVKVQVD, ; | (SEQ ID NO:32) |
| YKYQYDYKYQYDYKYQYD, ; | (SEQ ID NO:33) |
| HKHQHDHKHQHDHKHQHD, ; | (SEQ ID NO:34) |
| RARADADARARADADA, ; | (SEQ ID NO:35) |
| RADARGDARADARGDA, ; | (SEQ ID NO:36) |
| RAEARAEARAEARAEA, ; | (SEQ ID NO:37) |
| KADAKADAKADAKADA, ; | (SEQ ID NO:38) |
| AEAEAHAHAEAEAHAH, ; | (SEQ ID NO:39) |
| FEFEFKFKFEFEFKFK, ; | (SEQ ID NO:40) |
| LELELKLKLELELKLK, ; | (SEQ ID NO:41) |
| AEAEAKAKAEAEAKAK, ; | (SEQ ID NO:42) |
| AEAEAEAEAKAK, ; | (SEQ ID NO:43) |
| KAKAKAKAEAEAEAEA, ; | (SEQ ID NO:44) |
| AEAEAEAEAKAKAKAK, ; | (SEQ ID NO:45) |
| RARARARADADADADA, ; | (SEQ ID NO:46) |
| ADADADADARARARAR, ; | (SEQ ID NO:47) |
| DADADADARARARARA, ; | (SEQ ID NO:48) |
| HEHEHKHKHEHEHKHK, ; | (SEQ ID NO:49) |
| VEVEVEVEVEVEVEVEVE, ; and | (SEQ ID NO:50) |
| RFRFRFRFRFRFRFRFRF, . | (SEQ ID NO:51) |

It should be recognized that each of the peptides listed above includes a repeating sequence and that additional repeats can be included to extend the length of the peptides without destroying their ability to self-assemble. For example, the peptide AKAKAEAEAK AKAEAE (SEQ ID NO:1) has the repeating sequence AKAKAEAE (SEQ ID NO:52) and can be expressed as $(AKAKAEAE)_n$, (SEQ ID NO:52) where n=2. Longer peptides capable of self assembly can be made by increasing n with the caveat that the total number of amino acids in the final peptide cannot exceed 200. Preferred peptides are those having the following repeating structures: $(RARADADA)_n$ (SEQ ID NO:53) $(ARARADAD)_n$ (SEQ ID NO:89) $(RADARADA)_n$, (SEQ ID NO:54) and $(AEAEAKAK)_n$, (SEQ ID NO:55) in which n=2-10. Preferably, n=2-4 and more preferably, n=2.

Other peptides expressed in this manner and useful in the invention are: $(AKAKAEAE)_n$, (SEQ ID NO:52) where n=2-25; $(KAEA)_n$ (SEQ ID NO:56) where n=3-50; $(EAKA)_n$ (SEQ ID NO:57) where n=3-50; $(KAEA)_n$ (SEQ ID NO:58) where n=3-50; $(AEAK)_n$ (SEQ ID NO:59) where n=3-50; $(ADADARAR)_n$ (SEQ ID NO:60) where n=2-25; $(ARAD)_n$ (SEQ ID NO:61) where n=3-50; $(DARA)_n$ (SEQ ID NO:62) where n=3-50; $(RADA)_n$ (SEQ ID NO:63) where n=3-50; $(ADAR)_n$ (SEQ ID NO:64) where n=3-50; $(ARADAKAE)_n$ (SEQ ID NO:65) where n=2-25; $(AKAEARAD)_n$ (SEQ ID NO:66) where n=2-25; $(ARAKADAE)_n$ (SEQ ID NO:67) where n=2-25; $(KARAEADA)_n$ (SEQ ID NO:68) where n=2-25; $(AQ)_n$ where n=6-100; $(VQ)_n$ where n=6-100; $(YQ)_n$ where n=6-100; $(HQ)_n$ where n=6-100; $(AN)_n$ where n=6-100; $(VN)_n$ where n=6-100; $(YN)_n$ where n=6-100; $(HN)_n$ where n=6-100; $(ANAQ)_n$ (SEQ ID NO:69) where n=3-50; $(AQAN)_n$ (SEQ ID NO:70) where n=3-50; $(VNVQ)_n$ (SEQ ID NO:71) where n=3-50; $(VQVN)_n$ (SEQ ID NO:72) where n=3-50; $(YNYQ)_n$ (SEQ ID NO:73) where n=3-50; $(YQYN)_n$ (SEQ ID NO:74) where n=3-50; $(HNHQ)_n$ (SEQ ID NO:75) where n=3-50; $(HQHN)_n$ (SEQ ID NO:76) where n=3-50; $(AKAQAD)_n$ (SEQ ID NO:77) where n=2-33; $(VKVQVD)_n$ (SEQ ID NO:78) where n=2-33; $(YKYQYD)_n$ (SEQ ID NO:79) where n=2-33; $(HKHQHD)_n$ (SEQ ID NO:80) where n=2-33; $(RARADADA)_n$ (SEQ ID NO:53) where n=2-25; $(RADARGDA)_n$ (SEQ ID NO:81) where n=2-25; $(RAEA)_n$ (SEQ ID NO:82) where n=3-50; $(KADA)_n$ (SEQ ID NO:83) where n=3-50; $(AEAEAHAH)_n$ (SEQ ID NO:84) where n=2-25; $(FEFEFKFK)_n$ (SEQ ID NO:85) where n=2-25; $(LELELKLK)_n$ (SEQ ID NO:86) where n=2-25; $(AEAEAKAK)_n$ (SEQ ID NO:55) where n=2-25; $(AEAEAEAEAKAK)_n$ (SEQ ID NO:87) where n=1-16; $(KAKAKAKAEAEAEAEA)_n$ (SEQ ID NO:44) where n=1-12; $(AEAEAEAEAKAKAKAK)_n$ (SEQ ID NO:45) where n=1-12; $(RARARARADA DADADA)_n$ (SEQ ID NO:46) where n=1-12; $(ADADADADARARARAR)_n$ (SEQ ID NO:47) where n=1-12; $(DADADADARARARARA)_n$ (SEQ ID NO:48) where n=1-12; $(HEHEHKHK)_n$ (SEQ ID NO:88) where n=2-25; $(VE)_n$ where n=6-100; and $(RF)_n$ where n=6-100.

The biologically compatible membranes described above can be used in conjunction with any diagnostic or therapeutic agent, including peptides, nucleic acids (e.g., SiRNA), analgesics, anticancer drugs, cardiac drugs, growth factors, antibiotics, and drugs that promote wound healing, nerve growth or which can be used in the treatment of neurological disease. Specific agents include angiogenesis inhibitors, insulin-like growth factors, NSAIDs, endorphins or enkephalins, nerve growth factors, epidermal growth factor, erythropoietin, interleukins or interferons. The most preferred agent is insulin-like growth factor-1 (IGF-1).

The invention also includes a variety of methods for using the biologically compatible membranes discussed above. One of the main uses is in providing a support for the growth and differentiation of cells cultured in vitro. Preferred cells for culture are those of the cardiovascular system, including vascular endothelial cells, angioblasts, cardiac myoblasts, cardiac myocytes, and vascular smooth muscle cells. Other cells that can be cultured include bone marrow cells, periosteal cells, perichondrial cells, fibroblasts, skeletal myoblasts or myocytes, neuronal cells, hippocampal cells, epidermal cells, non-vascular endothelial cells or smooth muscle cells, keratinocytes, basal cells, embryonic, fetal or adult stem cells, lung cells, immune system cells, ovarian cells, pancreatic cells, cervical cells, liver cells, and foreskin cells. These cells may be obtained from established culture lines or they can be derived from a living organism. Culture may take place using standard media and techniques that are well known in the art. In each case, the biologically compatible peptide membrane used for support should be attached to an agent that promotes the growth or differentiation of the cultured cells. Examples of factors that may be attached include: vascular endothelial growth factor; granulocyte macrophage colony stimulating factor; angiopoietin 1 or 2; epidermal growth factor; nerve growth factor; transforming growth factor-beta; tumor necrosis factor-alpha; platelet-derived growth factor; insulin-like growth factor; acidic fibroblast growth factor; basic fibroblast growth factor; hepatocyte growth factor; brain-derived neurotrophic factor; keratinocyte growth factor; bone morphogenetic protein; and cartilage-derived growth factor.

The biologically compatible membrane provides a scaffold for cell growth and differentiation which can be implanted at various sites in the body as a therapeutic procedure. For example, cardiac endothelial cells or myocytes growing on a membrane with IGF-1 attached may be injected into the heart of a patient to repair damaged tissue. Similar types of procedures can be used for a wide variety of different tissues. For example, chondrocytes growing on a membrane might be implanted into a patient's knee to repair damaged cartilage, or neuronal cells growing on a matrix with attached nerve growth factor might be implanted in an effort to regenerate damaged neurons.

Apart from forming a scaffold for the growth of cells, the biologically compatible membranes may be used to maintain the delivery of a therapeutic agent at a specific site for a prolonged period of time. For example, angiogenesis inhibitors may be attached to membranes which are implanted at a site of tumor growth. Antibiotics can be attached to a membrane that is implanted at the site of a wound to prevent bacterial growth. In addition, membranes may be implanted in the body at sites that are relatively inaccessible to drugs administered systemically. For example, membranes may be implanted in the central nervous system to allow for the slow release of factors of potential value in the treatment of neural diseases.

In another aspect, the invention includes methods of making the biologically compatible membranes described above. This is accomplished by combining the self-assembling peptides in an aqueous medium containing sufficient monovalent metal cation to promote self assembly. Preferably, an aqueous solution containing a salt of the metal cation is formed first and peptides are then added to a final concentration of at least 1 mg/ml and preferably, at least 10 mg/ml. The concentration of monovalent metal cation can vary considerably but, in general, should be at least 5 mM. The upper limit for the cation is at least 3M but assembly of peptides has been reported to occur at concentrations as high as 5 M. Preferred cations include lithium, sodium and potassium. These may be provided as salts in conjunction with essentially any pharmaceutically acceptable anion, including chloride, acetate and phosphate. The use of divalent cations should be avoided as these appear to interfere with peptide assembly. Similarly, concentrations of detergent, such as sodium dodecyl sulfate (SDS) of 0.1% or higher, should generally be avoided.

DESCRIPTION OF THE INVENTION

The present invention is based upon the development of methodology that can be used for attaching compounds to self-assembling peptides and, ultimately, to the gel-like membranes that they form. The peptides themselves have been described in U.S. Pat. Nos. 5,670,483 and 6,548,630, both of which are hereby incorporated by reference. Essentially the same procedures described therein for making and using the peptides apply to the present invention. However, it has been found that factors can be non-covalently bound to the membranes formed by the self-assembling peptides provided that the percentage of peptides linked to these components remains relatively low, less than 10%. If the percentage increases above this, the attached compounds interfere with the assembly of peptides and membranes either do not form or do not form properly.

It has also been found that, as with other systems employing compounds attached using biotin/streptavidin, a spacer should be included between the peptide and the closest biotin attached to it. Spacers may also optionally be included between the attached factor and the biotin nearest to it. The result of the inclusion of the spacer or spacers is that the attached compound is separated from the peptide by at least an additional 12 angstroms. This can be accomplished by incorporating 1-15 fatty acids or amino acids between the peptide and attached factor with at least one of the fatty acids being between the peptide and biotin. Experiments have shown that when IGF-1 is attached to an implanted membrane, it remains at the implantation site for an extended period of time. Thus, membranes may be used as a scaffold for growing cells and factors promoting this growth can be maintained locally to promote this process.

Description of Peptides

The peptides used for self assembly should be at least 12 residues in length and contain alternating hydrophobic and hydrophilic amino acids. Peptides longer than about 200 amino acids tend to present problems with respect to solubility and membrane stability and should therefore be avoided. Ideally, peptides should be about 12-24 amino acids in length.

The self-assembling peptides must be complementary. This means that the amino acids on one peptide must be capable of forming ionic bonds or hydrogen bonds with the amino acids on another peptide. Ionic bonds would form between acidic and basic amino acid side chains. The hydrophilic basic amino acids include Lys, Arg, His, and Orn. The hydrophilic acidic amino acids are Glu and Asp. Ionic bonds would form between an acidic residue on one peptide and a basic residue on another. Amino acids that form hydrogen bonds are Asn and Gln. Hydrophobic amino acids that may be incorporated into peptides include Ala, Val, Ile, Met, Phe, Tyr, Trp, Ser, Thr, and Gly.

Self-assembling peptides must also be "structurally compatible." This means that they must maintain an essentially constant distance between one another when they bind. Interpeptide distance can be calculated for each ionized or hydrogen bonding pair by taking the sum of the number of unbranched atoms on the side-chains of each amino acid in the pair. For example, lysine has five and glutamic acid has four unbranched atoms on their side chains. An interaction between these two residues on different peptides would result in an interpeptide distance of nine atoms. In a peptide containing only repeating units of EAK, all of the ion pairs would involve lysine and glutamate and therefore a constant interpeptide distance would be maintained. Thus, these peptides would be structurally complementary. Peptides in which the variation in interpeptide distance varies by more than one atom (about 3-4 angstroms) will not form gels properly. For example, if two bound peptides have ion pairs with a nine-atom spacing and other ion pairs with a seven-atom spacing, the requirement of structural complementarity would not have been met. A full discussion of complementarity and structural compatibility may be found in U.S. Pat. Nos. 5,670, 483 and 6,548,630. The definitions used therein and examples provided apply equally with respect to the present invention.

It should also be recognized that membranes may be formed from either a homogeneous mixture of peptides or a heterogeneous mixture of peptides. The term "homogeneous" in this context means peptides that are identical with one another. "Heterogeneous" indicates peptides that bind to one another but which are structurally different. Regardless of whether homogenous or heterogeneous peptides are used, the requirements with respect to the arrangement of amino acids, length, complementarity, and structural compatibility apply. In addition, it should be recognized that the carboxyl and amino groups of the terminal residues of peptides can either be protected or not protected using standard groups.

Making of Peptides

The self-assembling peptides of the present invention can be made by solid-phase peptide synthesis using standard N-tert-butyoxycarbonyl (t-Boc) chemistry and cycles using n-methylpyrolidone chemistry. Biotin may be incorporated during peptide synthesis using standard methods. Alternatively, kits and reagents are commercially available (e.g., from Roche Applied Science) which contain the components (including spacers such as aminocaproic acid) needed for biotinylating both peptides and factors to be attached. Any of the procedures that have been described in the art with respect to the biotinylation of peptides can be applied to the present invention (see, e.g., Ohno, et al., *Biochem. Mol. Med.* 58:227-233 (1996); Smith, et al., *Proc. Natl. Acad. Sci. USA* 96:8855-8860 (1999)). Avidin or streptavidin has four sites for attaching to biotin and can serve to couple the biotinylated peptide to biotinylated drug.

Once peptides have been synthesized, they can be purified using procedures such as high pressure liquid chromatography on reverse-phase columns. Purity may also be assessed by HPLC and the presence of a correct composition can be determined by amino acid analysis.

Formation of Membranes

The self-assembling peptides described herein will not form membranes in water, but will assemble in the presence of a low concentration of monovalent metal cation. The order of effectiveness of these cations has been reported to be $Li^+>Na^+>K^+>Cs^+$ (U.S. Pat. No. 6,548,630). A concentration of monovalent cation of 5 mM should be sufficient for peptides to assemble and concentrations as high as 5 M should still be effective. The anion associated with the monovalent cation is not critical to the invention and can be acetate, chloride, sulfate, phosphate, etc.

The initial concentration of peptide will influence the final size and thickness of membranes formed. In general, the higher the peptide concentration, the higher the extent of membrane formation. Formation can take place in peptide concentrations as low as 0.5 mM or 1 mg/ml. However, membranes are preferably formed at higher initial peptide concentrations, e.g., 10 mg/ml, to promote better handling characteristics. Overall, it is generally better to form membrane by adding peptides to a salt solution rather than adding salt to a peptide solution.

The formation of membranes is relatively unaffected by pH or by temperature. Nevertheless, pH should be maintained below 12 and temperatures should generally be in the range of 4-90° C. Divalent metal cations at concentrations equal to or above 100 mM result in improper membrane formation and should be avoided. Similarly, a concentration of sodium dodecyl sulfate of 0.1% or higher should be avoided.

Membrane formation may be observed by simple visual inspection and this can be aided, if desired, using stains such as Congo Red. The integrity of membranes can also be observed microscopically, with or without stain.

Uses of Membranes

Previous work has established that membranes formed by self-assembling peptides can be seeded with cells and provide a matrix for their growth and differentiation. This process can be enhanced using the methodology described herein, i.e., by attaching appropriate growth factors to the membrane. For example, as discussed further herein, cardiac-specific insulin-like growth factor-1 (IGF-1) can be attached to membranes that are seeded with myocytes or endothelial cells. The seeded membrane can be maintained in culture or injected into the wall of a subject's heart to help in the growth or vascularization of new cardiac tissue. IGF-1 attached to membrane may also be implanted at sites of injury (e.g., the knee) to promote the growth of chondrocytes.

Apart from providing an environment for the growth of cells either in vitro or in vivo, the procedures described herein can be used for localizing drug delivery to a specific site in the body for an extended period of time. Essentially any type of drug can be attached to membranes including: analgesics; anticancer agents; proteins; growth factors; antiviral drugs; anti-metastasis drugs; antibiotics; cardiac drugs; beta blockers; ACE inhibitors; drugs that promote wound healing or nerve growth; anti-epileptics; drugs for Alzheimer's disease; immunosuppressive agents, etc. A non-exhaustive list of specific drugs includes: somatostatin; LHRH; NSAIDs such as naproxen; erythropoietin; interferons; interleukins; somatotropin; epidermal growth factor; heparin; endorphins/enkephalins; methotrexate; radioactive agents; angiogenesis inhibitors or promoters; nerve growth factor; insulin-like growth factors; erythromycin; streptomycin; and neomycin. Membranes having these drugs attached can be implanted at a specific site where they are needed. For example, membranes having anticancer agents attached (e.g., angiogenesis inhibitors) could be implanted at a site of tumor growth or a membrane with antibiotic attached could be implanted at a wound site to prevent infection. In addition, drugs may be attached to test their ability to promote healing at sites that may present problems with accessibility. For example, membranes may be implanted to allow for the slow release of factors of potential benefit in neural diseases.

EXAMPLES

IGF-1 is a potent cardiomyocyte growth and survival factor. Mice deficient in IGF-1 have increased apoptosis following myocardial infarction (Palmen, et al., *Cardiovasc. Res.* 50:516-524(2001)), while cardiac-specific IGF-1 overexpression protects against myocyte apoptosis and ventricular dilation following infarction (Li, et al., *J. Clin. Invest.* 100: 1991-1999(1997); Torella, et al., *Circ. Res.* 94:514-524 (2004)). IGF-1 overexpression increases cardiac stem cell number and growth, leading to an increase in myocyte turnover and function in the aging heart. Following infarction, IGF-1 promotes engraftment, differentiation, and functional improvement of embryonic stem cells transplanted into myocardium (Kofidis, et al., *Stem Cells* 22:1239-1245 (2004)). Furthermore, serum levels of IGF-1 correlate inversely with the risk of congenital heart failure in a subset of elderly patients (Vasan, et al., *Ann. Intern. Med* 139:642-648 (2003)). However, IGF-1 is a small protein that diffuses readily through tissues, a property that allows it to signal over great distances (Fraidenraich, et al., *Science* 306:247-252 (2004)) but also, as shown here, restricts the ability to deliver it to a tissue for prolonged periods.

Self-assembling peptides are oligopeptides comprised of alternating hydrophilic and hydrophobic amino acids (Zhang, *Nat. Biotechnol.* 21:1171-1178 (2003); Zhang, et al., *Proc.*

Nat'l Acad. Sci. USA 90: 3334-3338 (1993)). Upon exposure to physiological osmolarity and pH, the peptides rapidly assemble into small fibers (~10 nm) that can be injected into the myocardium to form 3-dimensional cellular microenvironments (Zhang, et al., *Curr. Opin. Chem. Biol.* 6:865-871 (2002); Davis, et al., *Circulation* 111:442-450 (2005)). These peptide microenvironments recruit a variety of cells including vascular cells.

The present example describes the development of a delivery system using a "Biotin Sandwich" approach that allows coupling of a factor to self-assembling peptides without interfering with self-assembly. Biotinylation of self-assembling peptides allowed specific and highly controlled delivery of IGF-1 (the Ea isoform) to local myocardial microenvironments, leading to improved results of cell therapy. Although we describe controlled myocardial delivery here, this approach may be used to delivery one factor or even multiple factors to other tissues for prolonged periods.

A. Materials and Methods

Self-Assembling Peptides

RAD16-II peptide (AcN-RARADADARARADADA-CNH2) (SEQ ID NO:35) was synthesized by Synpep (Dublin, Calif.). Biotinylated RAD16-II peptide was synthesized at the Massachusetts Institute of Technology by adding a biotin molecule linked to the peptide by 2 N-ε-Fmoc-ε-aminocaproic acid groups. Immediately prior to injection, to initiate self-assembly, peptides were dissolved in sterile sucrose (295 mM) at 1% (weight/volume) and sonicated for 10 minutes. For all biotinylated self-assembling peptide experiments, biotinylated and nonbiotinylated peptides were mixed in a 1:100 ratio prior to sonication.

Atomic Force Microscopy

Aliquots of 10 uL were removed from the peptide solution at various times after preparation and deposited on a freshly cleaved mica surface. To optimize the amount of peptide adsorbed, each aliquot was left on mica for up to 2 minutes and then rinsed with 50-100 μL of deionized water. Images were obtained by scanning the mica surface in air by an atomic force microscope (Multimode, Digital Instruments, Santa Barbara, Calif.) operating in tapping mode. Soft silicon cantilevers were chosen (FESP model, Digital Instrument, Santa Barbara, Calif.) with spring constant of 1-5 N/m and tip radius of curvature of 5-10 nm. Typical scanning parameters were as follows: tapping frequency ~70 KHZ, RMS amplitude before engage 1-1.2V, integral and proportional gains 0.5-0.7 and 0.8-1.0 respectively, setpoint 0.8-1 V, scanning speed 0.5-2 HZ.

Human IGF-1 ELISA

Injection regions were excised 5 minutes, 3, 7, 14, 28 and 84 days following peptide injection and snap frozen in liquid nitrogen. The samples were then homogenized in a buffer containing Tris-Triton and analyzed for human-specific IGF-1 content with a human-specific IGF-1 ELISA that has little cross-reactivity to other species (Diagnostic Systems Laboratories, Webster, Tex.).

Myocardial Infarction and Injection

Adult, male Sprague-Dawley rats weighing 250 grams were obtained from Charles River Laboratories (Wilmington, Mass.). The animals were anesthetized (60 mg/kg sodium pentobarbital) and, following tracheal intubation, the hearts were exposed by separation of the ribs. Myocardial infraction was performed as described previously. Immediately after exposure of the heart (non-infarct studies) or coronary artery ligation, cells alone or embedded within the self-assembling peptides (80 μL) were injected into the infarct zone through a 30-gauge needle while the heart was beating. Following injection, the chests were closed and animals were allowed to recover under a heating lamp. Echocardiograms were performed 1 and 21 days following surgery. The animal protocols were approved by the Harvard Medical School Standing Committee on Animals.

Neonatal Cardiomyocyte Isolation

One day old pups from Sprague-Dawley rats (Charles River Laboratories) were sacrificed and hearts were excised, washed in Hanks Buffered Salt Solution and, following mincing, were placed in trypsin (1 mg/ml) for 3 hours at 4° C. The resulting pellet was then dissolved in collagenase Type 2 (0.8 mg/ml) for 10 minutes at 37° C. The resulting pellet was resuspended in sucrose or self-assembling peptides for in vitro and in vivo studies. For in vivo infarction studies, the cells were incubated in suspension with an adenovirus for green fluorescent protein (GFP) or dominant negative Akt prior to embedding within the peptides.

Cell Culture Experiments

Neonatal cardiac myocytes were isolated as stated above and $10^6$ cells were suspended in 1% self-assembling peptides alone, with 10 ng/mL untethered or tethered IGF-1. Following assembly, cells were cultured in serum free media (DMEM, Invitrogen; Carlsbad, Calif.) for 14 days. Three-dimensional cultures were homogenized using Tri-Reagent (Sigma, St. Louis, Mo.) and protein extracted according to manufacturer's protocol for Western analysis and $^3$H-phenylalanine incorporation.

For adenovirus studies, cardiomyocytes were isolated and suspended in virus-containing serum free media for 2 hours. Cells were either collected for flow cytometry analysis, or plated on fibronectin-coated dishes and allowed to adhere for 24 hours. Biotin-IGF-1 was then added for 15 minutes and cells were harvested in 5× sample buffer for Western analysis.

Other Materials

Radiolabeled Streptavidin ($^{35}$S-SLR labeled) and $^3$H-phenylalanine were obtained from Amersham Biosciences (Piscataway, N.J.). Purified human IGF-1 and anti-human IGF-1 antibody, as well as the green membrane dye PKHGL-2 were obtained from Sigma. Purified Streptavidin was obtained from Pierce Biotechnology (Rockford, Ill.). Biotinylated IGF-1 was obtained from Immunological and Biochemical Testsystems (Reutlingen, Germany) and used at a final concentration of 10 ng/mL in all experiments. Antibodies to total and phospho-Akt, phospho-IGF-1 receptor, and cleaved caspase-3, were obtained from Cell Signaling Technology (Beverly, Mass.). Antibody to cardiac troponin I was obtained from Chemicon (Temecula, Calif.). Antibody to slow skeletal Troponin I was obtained from Santa Cruz Biotechnology (Santa Cruz, Calif.). Cy3-conjugated hemagglutinin antibody was obtained from Sigma.

B. Results

Selective Binding to Self-assembling Peptides through Streptavidin-biotin Linkages We have previously shown that biotinylated peptides can be synthesized and incorporated with self-assembling (Davis, et al., Circ Res 97: 8-15 (2005)). To allow sufficient distance from the peptide to allow streptavidin binding (Livnah, et al., *Proc Natl Acad Sci USA* 90:5076-5080 (1993); Pugliese, et al., *J. Mol Biol* 231:698-710 (1993)), the biotin was attached to the peptide by two N-εe-Fmoc-ε-aminocaproic acids. To determine the affinity for streptavidin binding to the biotinylated self-assembling peptides, we performed binding assays using $^{35}$S-streptavidin and 1:100 biotinylated peptides:nonbiotinylated peptides (1% final peptide weight/volume). These experiments demonstrated an apparent $K_d$ of $1.9 \times 10^{-7}$. Although this dissociation constant is substantially less than the dissociation constant for unbound biotin and streptavidin in solution, this result is consistent with previous reports of polymer conjugation and biotin-streptavidin affinity (Stayton, et al., *Nature* 378:472-474 (1995); Chan, et al., *Biomaterials* 24:559-570 (2003)). To further demonstrate streptavidin binding to the peptide fibers, we visualized the peptides with and without streptavidin using atomic force microscopy (AFM). The AFM images showed streptavidin bound to the biotinylated self-assembling peptides and the images of streptavidin were consistent with previously-published AFM images of streptavidin alone Neish, et al., *Br. J. Pharmacol* 135:1943-1950 (2002)). Taken together, these experiments show that streptavidin can be coupled to the biotinylated peptides in a specific manner.

"Biotin Sandwich" for Tethering of IGF-1 to the Peptide Fibers

We next developed a "biotin sandwich" method for targeting IGF-1 to the peptides, taking advantage of the four binding sites available on streptavidin. Biotinylated IGF-1 and streptavidin were mixed in a 1:1 molar ratio, allowing other biotin-binding sites on most tetravalent streptavidins to remain available for binding to the biotinylated self-assembling peptides. To test this method, we incubated biotinylated IGF-1 bound to streptavidin with either biotinylated or non-biotinylated self-assembling peptides for 1 hour. IGF-1 protein was found to bind to biotinylated peptides. Identical results were obtained when IGF-1 was mixed with the peptides during self-assembly or added after the self-assembly had occurred. These data confirm that the biotin sandwich method for delivery of IGF-1 is feasible.

Biotinylated IGF-1 is Active and Promotes Cell Survival and Maturation in 3D Culture To verify that biotinylation of IGF-1 did not interfere with bioactivity, we treated rat neonatal cardiac myocytes with biotinylated IGF-1 or non-biotinylated IGF-1 and examined Akt phosphorylation, a downstream target of IGF-1 signaling. Biotinylated IGF-1 induced Akt phosphorylation to the same degree as non-biotinylated IGF-1. These data suggest that specific targeting of IGF-1 can be achieved with the biotinylated IGF-1 "biotin sandwich" method without interfering with bioactivity.

To test the biological effect of prolonged IGF-1 delivery, we cultured rat neonatal cardiac myocytes in self-assembling peptides alone, peptides with untethered IGF-1 (b-IGF-1+streptavidin+nonbiotinylated peptides) and peptides with tethered IGF-1 (b-IGF+streptavidin+biotinylated peptides) for 14 days. Phosphorylation of Akt was detectable only in the tethered IGF-1 samples, with no changes in overall Akt levels. Furthermore, tethered IGF-1 reduced cleavage of caspase-3, a marker of apoptosis. In addition, tethered IGF-1 altered expression of troponin I isoforms. During maturation, there is a switch in troponin I isoforms in the heart from slow skeletal troponin I to cardiac troponin I (Gao, et al., *J. Mol. Cell Cardiol.* 27:541-550 (1995)). Tethering of IGF-1 decreased slow skeletal troponin I and increased cardiac troponin I. These data demonstrate that IGF-1 tethered through the biotin sandwich method promotes long-term activation of survival pathways and increases the expression of cardiac maturation markers. Furthermore, to determine if neonatal myocytes cultured for extended periods of time in peptides containing tethered IGF-1 still induce new protein synthesis, $^3$H-phenylalanine incorporation was measured. Tethered IGF-1 was found to increase new protein synthesis after 14 days compared to untethered IGF-1 or peptides alone.

Tethered IGF-1 can be Delivered In Vivo and is Bioactive

Next, we sought to determine whether specific delivery of IGF-1 with self-assembling peptides could be achieved in vivo for extended periods of time. 25 ng of free non-biotinylated human IGF-1 (negative control), biotinylated human IGF-1 bound to streptavidin in nonbiotinylated peptides (untethered IGF-1, negative control), or tethered IGF-1 with streptavidin coupled to biotinylated self-assembling peptides was injected into the myocardium of rats (n≧4 for each group/time point). Five minutes after injection, the human IGF-1 detected by species-specific ELISA was not different between groups. After 3 days, only 1.97±1.18 ng of free IGF-1 remained, whereas 8.08±0.60 ng of tethered IGF-1 bound to the biotinylated nanofibers was detected (p<0.01). After 7, 14 and 28 days, tethered IGF-1 that was bound to the biotinylated nanofibers far exceeded the negligible amounts in the control groups. This specific targeted delivery of IGF-1 was not observed with control peptides lacking biotin. After 3 months, however, there was a reduction in remaining IGF-1 in the tethered group with levels comparable to controls. To demonstrate in vivo biological activity of IGF-1 delivery, myocardial tissues 14 days post-injection were stained for phospho-Akt. Activation of Akt was detected in tissues with tethered IGF-1 but not in control tissues without tethered IGF-1.

Tethered IGF-1 Reduces Implanted Cardiomyocyte Apoptosis and Increases Cell Growth To determine the effects of tethered IGF-1 on transplanted cells, isolated neonatal cardiac myocytes were labeled with the membrane dye PKHGL-2 and 50,000 cells were embedded within self-assembling peptides containing no IGF-1, untethered IGF-1 or tethered IGF-1. Tissues were harvested 14 days after myocardial injection (n=5 animals/group, randomized and blinded). Tethered IGF-1 significantly reduced the percentage of implanted cells positive for the apoptotic marker cleaved caspase-3 (31.1%±1.75% vs. 21.93%±2.20%, n>160 cells/group; p<0.01, ANOVA followed by Dunnett's test). Additionally, in a separate randomized and blinded study size of GFP-positive implanted cells, the cross-sectional area of cardiomyocytes injected with tethered IGF-1 was 25% greater than injected cells with no IGF-1 or untethered IGF-1 (16.3±0.56 µm$^2$ vs. 21.67±0.79 µm$^2$, n≧300 cells/group; p<0.01, ANOVA followed by Dunnett's test). These data demonstrate that IGF-1 can be delivered specifically to the myocardium with biotinylated self-assembling peptides and that this delivery activates critical survival pathways and improves transplanted cell growth.

Tethered IGF-1 Improves Cell Therapy after Experimental Myocardial Infarction

To determine if tethered IGF-1 in the absence of cell therapy improves cardiac function after injury, we performed a blinded and randomized myocardial infarction study in 37 rats. IGF-1 alone, self-assembling peptides alone, and self-assembling peptides with or without tethered IGF-1 were injected into the infarct zone immediately after occlusion. Echocardiograms 1 day and 21 days following infarction showed no differences in cardiac function (fractional shortening, wall thickness, end diastolic diameter) among the treatment groups. This null in vivo finding in the absence of cells was not surprising; we anticipated that isolated injected microenvironments with tethered IGF-1 in the absence of cells would have no beneficial effect on cardiac function.

In contrast, we hypothesized that inclusion of cells with IGF-1 would improve systolic function after infarction. We performed another randomized and blinded infarct study in 36 rats; 500,000 neonatal cardiomyocytes marked with a adenovirus encoding GFP were injected alone, injected with self-assembling peptides, or injected with self-assembling peptides containing untethered or tethered IGF-1 following myocardial infarction. Additionally, cells infected with a hemagglutinin-tagged dominant negative Akt adenovirus (Fujio Y, et al., *J. Biol. Chem.* 274: 16349-16354 (1999;

"dnAkt") were also injected with self-assembling peptides containing tethered IGF-1 and injected following myocardial infarction. GFP and dnAkt infection rates were 95-100% and isolated neonatal myocytes infected with dnAkt had no phosophorylation of Akt in response to IGF-1 treatment, despite activation of the IGF-1 receptor. There was no significant effect of any treatment at 1 day post-infarction. However, after 21 days, the tethered IGF-1 cell therapy group had significantly improved fractional shortening as compared to all other treatments. To determine if targeted IGF-1 delivery attenuates ventricular dilation, left ventricular end diastolic diameter was measured after 21 days and compared to day 1 post-infarction. There was the anticipated ventricular dilation in the infarcted control rats. Tethered IGF-1 attenuated ventricular dilation compared to untethered IGF-1, and this benefit was blocked by the dominant negative Akt adenovirus. A separate two-dimensional analysis of ventricular volume (modified Simpson's method) also showed that progressive dilation after infarction was attenuated by self-assembling peptide delivery of tethered IGF-1. Immunofluorescent staining for tropomyosin co-localized with GFP demonstrated increased cell size in the tethered IGF-1 group. These data demonstrate that tethered IGF-1 improves the efficacy of cell therapy following infarction, improving ventricular function and preventing post-infarction ventricular dilation.

C. Discussion

In this example, we demonstrate that self-assembling peptides can provide specific and prolonged local myocardial delivery of a survival factor, IGF-1, using tetravalent streptavidin and biotinylated self-assembling peptides. Delivery was highly controllable and the precision with this approach may represent a major advantage compared with gene therapy approaches. Local delivery of IGF-1 increased cardiomyocyte growth both in vitro and in vivo, and this effect was consistent with an improvement in cell therapy efficacy following experimental infarction.

We designed the biotin sandwich method to deliver IGF-1 with biotinylated peptides in order to maximize the probability of self-assembly and thus retention in the myocardium. Streptavidin and biotin-IGF-1 were combined in equimolar ratios and added to the biotinylated peptides. Since streptavidin contains 4 biotin binding sites, the majority of biotin-IGF-1-streptavidin complexes have additional unoccupied sites to bind to the biotin moiety on the peptides. For this strategy, it was critical to show that the biotinylation of IGF-1 did not compromise bioactivity. Tethered IGF-1 remained capable of induction of phosphorylation of Akt, a downstream mediator of IGF-1 signaling, in cardiomyocytes. In addition, tethered IGF-1 peptides promoted cardiomyocyte maturation, as measured by a switch in cardiac troponin I isoforms and increased protein synthesis.

By using a human-specific IGF-1 assay, we were able to quantify IGF-1 delivery in vivo. We found that free IGF-1 was rapidly eliminated from the myocardium, presumably through convective loss through capillaries or lymphatics. Embedding the IGF-1 in nonbiotinylated peptides (untethered IGF-1) increased IGF-1 retention at early time points, consistent with some nonspecific binding to the peptide fibers, but only tethered IGF-1 was delivered at later time points. Additionally, the tethered IGF-1 was still active in vivo, resulting in detectable levels of phospho-Akt after 14 days. Tethered IGF-1 in the absence of cells did not protect cardiac function following myocardial infarction in a randomized and blinded study. We speculate that tethered IGF-1 is not able to diffuse out of the peptide microenvironment and protect nearby myocytes. Supporting this hypothesis is our finding that phosphorylation of Akt was detectable only within the peptide microenvironment and not in surrounding myocardium.

However, when combined with cell therapy, tethered IGF-1 reduced the cleavage of caspase-3 and increased the size of transplanted myocytes. These effects of tethered IGF-1 on implanted cells resulted in improved systolic function 21 days following infarction. Tethered IGF-1 combined with cell therapy was not only able to improve fractional shortening, but reduced ventricular dilation as measured by two different methods. Activation of Akt was critical to this recovery as cells infected with a dominant negative Akt adenovirus did not restore function, even in the presence of tethered IGF-1. It is important to note, however, that we used a small number of cells (500,000) relative to the millions of cardiomyocytes lost in myocardial infarction in the rat. Thus, it is highly unlikely that improved systolic function with tethered IGF-1 was due to a direct contribution of transplanted cells to contractile function.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A biologically compatible peptide membrane comprising self-assembling peptides wherein:
   (a) said peptides are 12-200 amino acids in length, have alternating hydrophobic and hydrophilic amino acids, are complementary and are structurally compatible; and
   (b) 0.1-10% of said peptides are bound to a factor by a biotin/streptavidin linkage, wherein there is a spacer separating said factor from said peptide by at least 14 angstroms and no more than 250 angstroms and wherein said factor is an insulin-like growth factor that retains biological activity.

2. The biologically compatible peptide membrane of claim 1, wherein said peptides are 12-24 amino acids in length.

3. The biologically compatible peptide membrane of claim 1, wherein said spacer is a chain of 1-10 fatty acids.

4. The biologically compatible peptide membrane of claim 1, wherein said spacer is a chain of 1-10 amino acids.

5. The biologically compatible peptide membrane of claim 1 wherein said peptides are homogeneous.

6. The biologically compatible peptide membrane of claim 1 wherein said peptides are selected from the group consisting of:

| Sequence | |
|---|---|
| AKAKAEAEAKAKAEAE,; | (SEQ ID NO:1) |
| AKAEAKAEAKAEAKAE,; | (SEQ ID NO:2) |
| EAKAEAKAEAKAEAKA,; | (SEQ ID NO:3) |
| KAEAKAEAKAEAKAEA,; | (SEQ ID NO:4) |
| AEAKAEAKAEAKAEAK,; | (SEQ ID NO:5) |
| ADADARARADADARAR,; | (SEQ ID NO:6) |
| ARADARADARADARAD,; | (SEQ ID NO:7) |
| DARADARADARADARA,; | (SEQ ID NO:8) |
| RADARADARADARADA,; | (SEQ ID NO:9) |
| ADARADARADARADAR,; | (SEQ ID NO:10) |
| ARADAKAEARADAKAE,; | (SEQ ID NO:11) |
| AKAEARADAKAEARAD,; | (SEQ ID NO:12) |
| ARAKADAEARAKADAE,; | (SEQ ID NO:13) |

-continued

| | |
|---|---|
| AKARAEADAKARADAE,; | (SEQ ID NO:14) |
| AQAQAQAQAQAQAQAQ,; | (SEQ ID NO:15) |
| VQVQVQVQVQVQVQVQ,; | (SEQ ID NO:16) |
| YQYQYQYQYQYQYQYQ,; | (SEQ ID NO:17) |
| HQHQHQHQHQHQHQHQ,; | (SEQ ID NO:18) |
| ANANANANANANANAN,; | (SEQ ID NO:19) |
| VNVNVNVNVNVNVNVN,; | (SEQ ID NO:20) |
| YNYNYNYNYNYNYNYN,; | (SEQ ID NO:21) |
| HNHNHNHNHNHNHNHN,; | (SEQ ID NO:22) |
| ANAQANAQANAQANAQ,; | (SEQ ID NO:23) |
| AQANAQANAQANAQAN,; | (SEQ ID NO:24) |
| VNVQVNVQVNVQVNVQ,; | (SEQ ID NO:25) |
| VQVNVQVNVQVNVQVN,; | (SEQ ID NO:26) |
| YNYQYNYQYNYQYNYQ,; | (SEQ ID NO:27) |
| YQYNYQYNYQYNYQYN,; | (SEQ ID NO:28) |
| HNHQHNHQHNHQHNHQ,; | (SEQ ID NO:29) |
| HQHNHQHKHQHNHQHN,; | (SEQ ID NO:30) |
| AKAQADAKAQADAKAQAD,; | (SEQ ID NO:31) |
| VKVQVDVKVQVDVKVQVD,; | (SEQ ID NO:32) |
| YKYQYDYKYQYDYKYQYD,; | (SEQ ID NO:33) |
| HKHQHDHKHQHDHKHQHD,; | (SEQ ID NO:34) |
| RARADADARARADADA,; | (SEQ ID NO:35) |
| RADARGDARADARGDA,; | (SEQ ID NO:36) |
| RAEARAEARAEARAEA,; | (SEQ ID NO:37) |
| KADAKADAKADAKADA,; | (SEQ ID NO:38) |
| AEAEAEAHAEAEAHAH,; | (SEQ ID NO:39) |
| FEFEFKFKFEFEFKFK,; | (SEQ ID NO:40) |
| LELELKLKLELELKLK,; | (SEQ ID NO:41) |
| AEAEAKAKAEAEAKAK,; | (SEQ ID NO:42) |
| AEAEAEAEAKAK,; | (SEQ ID NO:43) |
| KAKAKAKAEAEAEAEA,; | (SEQ ID NO:44) |
| AEAEAEAEAKAKAKAK,; | (SEQ ID NO:45) |
| RARARARADADADADA,; | (SEQ ID NO:46) |
| ADADADADARARARAR,; | (SEQ ID NO:47) |
| DADADADARARARARA,; | (SEQ ID NO:48) |
| HEHEHKHKHEHEHKHK,; | (SEQ ID NO:49) |
| VEVEVEVEVEVEVEVE,; and | (SEQ ID NO:50) |
| RFRFRFRFRFRFRFRF,. | (SEQ ID NO:51) |

7. The biologically compatible peptide membrane of claim 1, wherein said peptides are homogeneous and have a structure selected from the group consisting of: (RARADADA)$_n$ SEQ ID NO:53; (ARARADAD)$_n$ SEQ ID NO:89; and (RADARADA)$_n$ SEQ ID NO:54, wherein n=2-10.

8. The biologically compatible membrane of claim 7, wherein n=2-4.

9. The biologically compatible membrane of claim 7, wherein n=2.

10. The biologically compatible peptide membrane of claim 1, wherein said peptides are homogeneous and have the structure (AEAEAKAK)$_n$ SEQ ID NO:55, wherein n=2-10.

11. The biologically compatible peptide membrane of claim 1, wherein said factor is insulin-like growth factor-1.

12. A method of culturing cells in vitro comprising growing said cells in culture medium on the biologically compatible membrane of claim 1.

13. The biologically compatible peptide membrane of claim 11, wherein said peptides are 12-24 amino acids in length.

14. The biologically compatible peptide membrane of claim 13, wherein said spacer is a chain of 1-10 fatty acids or 1-10 amino acids and wherein said peptides are homogeneous.

15. The biologically compatible peptide membrane of claim 14, wherein said peptides are selected from the group consisting of:

| | |
|---|---|
| AKAKAEAEAKAKAEAE, | (SEQ ID NO:1); |
| AKAEAKAEAKAEAKAE, | (SEQ ID NO:2); |
| EAKAEAKAEAKAEAKA, | (SEQ ID NO:3); |
| KAEAKAEAKAEAKAEA, | (SEQ ID NO:4); |
| AEAKAEAKAEAKAEAK, | (SEQ ID NO:5); |
| ADADARARADADARAR, | (SEQ ID NO:6); |
| ARADARADARADARAD, | (SEQ ID NO:7); |
| DARADARADARADARA, | (SEQ ID NO:8); |
| RADARADARADARADA, | (SEQ ID NO:9); |
| ADARADARADARADAR, | (SEQ ID NO:10); |
| ARADAKAEARADAKAE, | (SEQ ID NO:11); |
| AKAEARADAKAEARAD, | (SEQ ID NO:12); |
| ARAKADAEARAKADAE, | (SEQ ID NO:13); |
| AKARAEADAKARADAE, | (SEQ ID NO:14); |
| AQAQAQAQAQAQAQAQ, | (SEQ ID NO:15); |
| VQVQVQVQVQVQVQVQ, | (SEQ ID NO:16); |
| YQYQYQYQYQYQYQYQ, | (SEQ ID NO:17); |
| HQHQHQHQHQHQHQHQ, | (SEQ ID NO:18); |
| ANANANANANANANAN, | (SEQ ID NO:19); |
| VNVNVNVNVNVNVNVN, | (SEQ ID NO:20); |
| YNYNYNYNYNYNYNYN, | (SEQ ID NO:21); |
| HNHNHNHNHNHNHNHN, | (SEQ ID NO:22); |
| ANAQANAQANAQANAQ, | (SEQ ID NO:23); |
| AQANAQANAQANAQAN, | (SEQ ID NO:24); |

-continued

| | |
|---|---|
| VNVQVNVQVNVQVNVQ, | (SEQ ID NO:25); |
| VQVNVQVNVQVNVQVN, | (SEQ ID NO:26); |
| YNYQYNYQYNYQYNYQ, | (SEQ ID NO:27); |
| YQYNYQYNYQYNYQYN, | (SEQ ID NO:28); |
| HNHQHNHQHNHQHNHQ, | (SEQ ID NO:29); |
| HQHNHQHNHQHNHQHN, | (SEQ ID NO:30); |
| AKAQADAKAQADAKAQAD, | (SEQ ID NO:31); |
| VKVQVDVKVQVDVKVQVD, | (SEQ ID NO:32); |
| YKYQYDYKYQYDYKYQYD, | (SEQ ID NO:33); |
| HKHQHDHKHQHDHKHQHD, | (SEQ ID NO:34); |
| RARADADARARADADA, | (SEQ ID NO:35); |
| RADARGDARADARGDA, | (SEQ ID NO:36); |
| RAEARAEARAEARAEA, | (SEQ ID NO:37); |
| KADAKADAKADAKADA, | (SEQ ID NO:38); |
| AEAEAHAHAEAEAHAH, | (SEQ ID NO:39); |
| FEFEFKFKFEFEFKFK, | (SEQ ID NO:40); |
| LELELKLKLELELKLK, | (SEQ ID NO:41); |
| AEAEAKAKAEAEAKAK, | (SEQ ID NO:42); |
| AEAEAEAEAKAK, | (SEQ ID NO:43); |
| KAKAKAKAEAEAEAEA, | (SEQ ID NO:44); |
| AEAEAEAEAKAKAKAK, | (SEQ ID NO:45); |
| RARARARADADADADA, | (SEQ ID NO:46); |
| ADADADADARARARAR, | (SEQ ID NO:47); |
| DADADADARARARARA, | (SEQ ID NO:48); |
| HEHEHKHKHEHEHKHK, | (SEQ ID NO:49); |
| VEVEVEVEVEVEVEVEVE, | (SEQ ID NO:50); and |
| RFRFRFRFRFRFRFRFRERF, | (SEQ ID NO:51). |

16. The biologically compatible peptide membrane of claim 11, wherein said peptides are homogeneous and have a structure selected from the group consisting of: (RARADADA)$_n$ SEQ ID NO:53; (ARARADAD)$_n$ SEQ ID NO:89; and (RADARADA)$_n$ SEQ ID NO:54, wherein n=2-10.

17. The biologically compatible membrane of claim 16, wherein n=2-4 and said spacer is a chain of 1-10 fatty acids or 1-10 amino acids.

* * * * *